(12) United States Patent
Schaenzlin et al.

(10) Patent No.: US 8,248,076 B2
(45) Date of Patent: Aug. 21, 2012

(54) DEVICE AND METHOD FOR MEASURING EXHAUST GAS WITH CHARGED PARTICLES

(75) Inventors: Katharina Schaenzlin, Rottenburg-Obernau (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 788 days.

(21) Appl. No.: 11/993,295

(22) PCT Filed: May 9, 2006

(86) PCT No.: PCT/EP2006/062144
§ 371 (c)(1),
(2), (4) Date: Dec. 20, 2007

(87) PCT Pub. No.: WO2007/000368
PCT Pub. Date: Jan. 4, 2007

(65) Prior Publication Data
US 2010/0192670 A1    Aug. 5, 2010

(30) Foreign Application Priority Data
Jun. 27, 2005 (DE) .................. 10 2005 029 834

(51) Int. Cl.
    *G01N 27/62*    (2006.01)
(52) U.S. Cl. .......................................... 324/464
(58) Field of Classification Search .......... 324/459, 324/464
    See application file for complete search history.

(56) References Cited

U.S. PATENT DOCUMENTS

| | | | | |
|---|---|---|---|---|
| 3,679,973 A * | 7/1972 | Smith et al. | ........... | 324/71.1 |
| 3,700,330 A | 10/1972 | Davis | | |
| 3,718,029 A * | 2/1973 | Gourdine et al. | ........... | 73/28.02 |
| 4,074,572 A * | 2/1978 | Bullis et al. | ........... | 73/861.09 |
| 4,167,114 A * | 9/1979 | Zizine | ........... | 73/861.09 |
| 4,922,714 A * | 5/1990 | Grob et al. | ........... | 60/276 |
| 4,976,154 A | 12/1990 | Schneider et al. | | |
| 5,009,064 A * | 4/1991 | Grob et al. | ........... | 60/276 |
| 5,317,271 A * | 5/1994 | Wentworth et al. | ........... | 324/464 |
| 5,394,091 A * | 2/1995 | Wentworth et al. | ........... | 324/464 |
| 5,892,364 A * | 4/1999 | Monagle | ........... | 324/464 |
| 6,418,780 B1 * | 7/2002 | Chon | ........... | 73/23.32 |
| 2004/0245993 A1 * | 12/2004 | Bonne | ........... | 324/464 |
| 2008/0041138 A1 * | 2/2008 | Marra | ........... | 73/31.02 |

FOREIGN PATENT DOCUMENTS

| | | |
|---|---|---|
| DE | 3627162 A1 | 2/1988 |
| DE | 19853841 A1 | 6/1999 |
| DE | 10242301 A1 | 3/2004 |
| GB | 1105604 | 3/1968 |
| WO | 03034053 A2 | 4/2003 |

OTHER PUBLICATIONS

English Translation of International Written Report.*
Machine Translation of WO 03/034053. Translation acquired on Jul. 18, 2010.*

* cited by examiner

*Primary Examiner* — Lisa Caputo
*Assistant Examiner* — Punam Roy
(74) *Attorney, Agent, or Firm* — Ronald E. Greigg

(57) ABSTRACT

The invention relates to a device used to measure exhaust gas having ionised particles in a motor vehicle. The device comprises an ionising device which includes an electrode arrangement and a charge measuring device. The electrode arrangement comprises at least one pair of electrodes including at least one electrode and at least one counter electrode. A dielectric is arranged between the electrode and the counter electrode in order to generate a dielectrically impeded discharge. The invention also relates to a corresponding method.

13 Claims, 2 Drawing Sheets

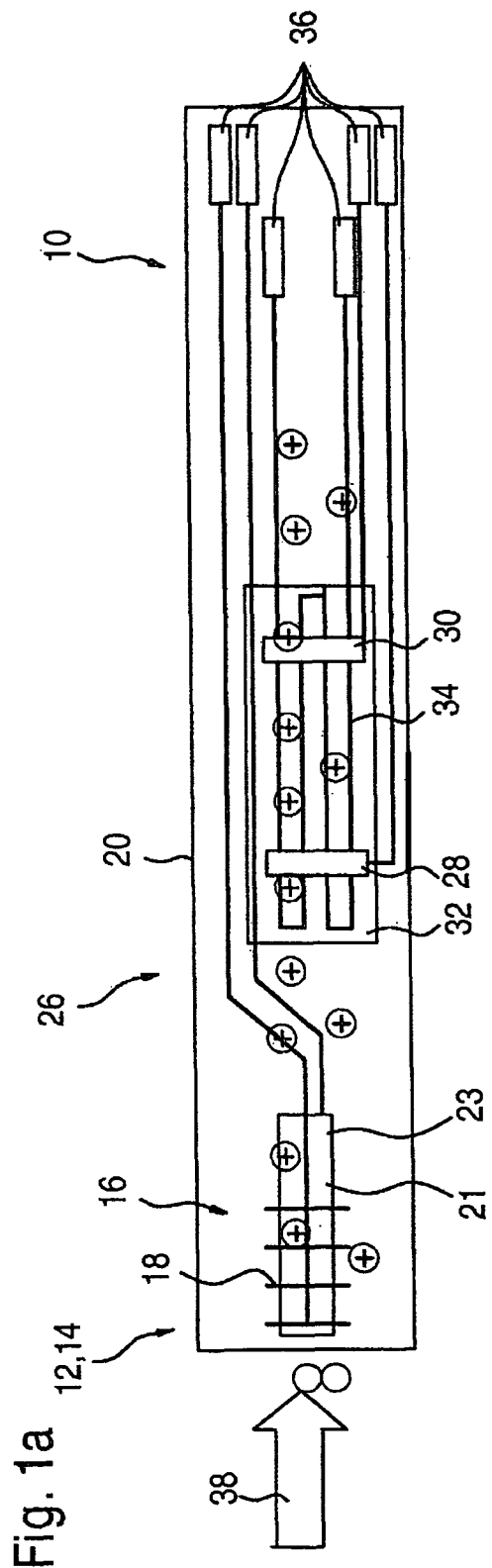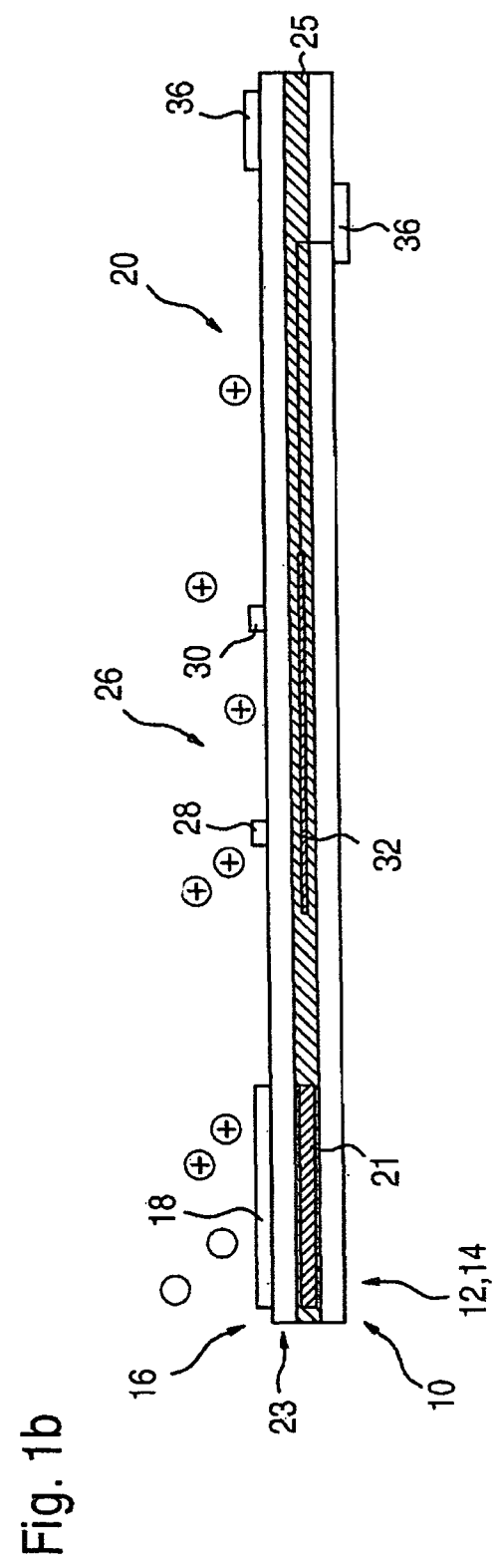
Fig. 1a
Fig. 1b

DEVICE AND METHOD FOR MEASURING EXHAUST GAS WITH CHARGED PARTICLES

CROSS-REFERENCE TO RELATED APPLICATION

This application is a 35 USC 371 application of PCT/EP 2006/062144 filed on May 9, 2006.

BACKGROUND OF THE INVENTION

1. Field of the Invention

The invention relates to an improved method of and apparatus for measuring exhaust gas with charged particles, in particular in a motor vehicle.

2. Prior Art

Devices for measuring exhaust gas with charged particles are known in the prior art. They are used in conjunction with combustion processes, especially in motor vehicles. Besides the determination of chemical components such as oxygen or carbon dioxide, it is important to obtain measurements of the particle concentration, the exhaust gas quantity, or the exhaust gas flow speed, so as to make optimal variation of the combustion process possible. It is also known at present, in motors, to employ external exhaust gas recirculation to reduce the emissions of nitrogen oxides. To make it possible for the parameters of the exhaust gas to be determined as precisely as possible, direct measurement in the exhaust gas course is advantageous. The often-used hot-film air flow rate meter can be employed under only very limited conditions here, however, since it is only limitedly tolerant of soiling from exhaust gas. It must be noted that if the exhaust gas recirculation rate is determined with an error of even only about 1%, the result can be miscalculation of the $NO_x$ or soot emissions of approximately 3% to 5%. Moreover, with large volumetric throughputs, it is more difficult to implement the hot-film air flow rate meter. A good principle for solving the problem of determining particles in the exhaust gas stream is shown in German Patent Disclosure DE 102 42 301 A1, where an ionizing device charges particles in the exhaust gas stream, and these charged particles are detected downstream in the exhaust gas stream by a charge measuring device. The more charged particles are detected, the higher the particle concentration.

SUMMARY AND ADVANTAGES OF THE INVENTION

In a device for measuring exhaust gas with charged particles, in particular in a motor vehicle, having an ionizing device with an electrode arrangement and a charge measuring device, in which the electrode arrangement has at least one pair of electrodes having at least one electrode and at least one counterelectrode, it is proposed according to the invention that in order to effect a dielectrically impeded discharge between the electrode and the counterelectrode, a dielectric is provided. The result is a compact device that is advantageous in terms of energy, and with which the exhaust gas flow speed and/or the exhaust gas quantity, in particular, can be measured. The term "particle" should be understood broadly; in particular, this term includes particles, gas molecules, and ions. The task of the ionizing device is to enrich the exhaust gas, by the targeted generation of free charge carriers, with ions and/or charged molecules and/or particles, or in other words in general, with charged particles. In a charge measuring device downstream of the ionizing device these charged particles, which are entrained with the exhaust gas stream, are then detected. Since the charge measuring device detects charged particles in general, it is not necessary that particles be present. Because of the dielectrically impeded discharge, no current, or only a negligible flow of current, occurs between the electrode and the counterelectrode, so that only little energy is consumed. Hence the invention is distinguished in particular from charging methods using an arc, in which a considerable flow of current and major energy consumption occur. For details with regard to the evaluation of the measurements, see DE 102 42 301 A1, referred to above, and German Patent DE 36 27 162 C2. With the proposed device, both the time of flight of the particles between the ionizing device and the charge measuring device, and thus the exhaust gas flow speed, and the exhaust gas volumetric flow can be determined quite precisely. The device is also suitable for use with large volumetric flows, of the kind encountered in utility vehicles, for instance. Because of the measured values ascertained, the exhaust gas recirculation rate can be determined precisely, and the emissions values of engines can be improved. With respect to the precision made possible, the proposed device is moreover a favorable solution to the problem described.

Advantageously, the ionizing device and/or the charge measuring device is embodied on and/or inside at least one ceramic element. In this way, the device can be used especially well even in exhaust gas flows that are at a high temperature and/or high pressure. Thus the required electrical connection points can also be realized on the ceramic element, for instance as terminal pads. This contributes to a compact structural form, especially in the form of a module.

Preferably, at least portions of the ionizing device and of the charge measuring device are embodied on and/or inside a common ceramic element. Thus the electrode in particular can be disposed on one ceramic element, and the counterelectrode and the charge measuring device can be disposed on a further ceramic element.

In a refinement of the invention, a first ceramic element and a second ceramic element, spaced apart from it, are embodied as an exhaust gas conductor. It is thus assured that the exhaust gas, having been charged by the ionizing device, reaches the charge measuring device for correct measurement and, after being charged, does not flow past the charge measuring device in a considerable amount and at too great a distance from it.

Advantageously, the device has at least one heating element, in particular a heating coil. As a result, soiling of the device from deposits can be counteracted. If the heating element is sintered in place as a heating coil, then not only is especially effective heating attained, but also a very sturdy structural form is attained.

It is furthermore preferred if the heating element is disposed in the region of the charge measuring device. Precisely in the region of the charge measuring device, especially in the case of electrostatic electrodes, soot deposits need to be avoided. For that purpose, the region is heated to a temperature above the soot deposition temperature. A deposit or condensation of soot particles can thus be avoided, and thus even short circuits from deposits between a plurality of electrostatic electrodes can be specifically prevented.

Advantageously, the electrode and the counterelectrode each extend two-dimensionally. While in principle the (counter-) electrode can also be embodied as an antenna, especially good charging is obtained as a result of this embodiment of the electrode and the counterelectrode.

In a preferred embodiment, the ionizing device has a spark generator, in particular on the spark plug principle. As a result, it is possible to generate free charge carriers in a simple and economical way. Precisely in a motor vehicle, the ignition voltage can be furnished especially easily, since the spark generator can be based here on the same principle as that of a spark plug.

It is advantageous if the device is disposed in an exhaust gas tract. As a result, the ionizing device and the charge measuring device can be designed in manifold ways. By the use of the exhaust gas tract, it is always assured that the proportion of exhaust gas having the charge carriers generated is also carried to the charge measuring device.

Moreover, the invention relates to a method for measuring exhaust gas with charged particles, in particular in a motor vehicle, in which particles contained in the exhaust gas are charged by means of an ionizing device, and the charged particles are detected by means of a charge measuring device, and according to the invention the particles are charged by means of a dielectrically impeded discharge.

It is advantageous if on the basis of a fixed spacing between the ionizing device and the charge measuring device, a flow speed of the exhaust gas is determined by means of an evaluation device. To that end, the time in which the charged particles from the ionizing device reach the charge measuring device is measured, and the flow speed is calculated from the quotient of the distance and the time. Alternatively or optionally as an additional measurement it is possible to provide a plurality of measuring elements, in particular a plurality of electrostatic electrodes, in the charge measuring device. Then the motions of the charged particles between the measuring elements and/or between the ionizing device and the various measuring elements can also be ascertained. The various distances are selected such that on the one hand they are great enough to attain adequate resolution chronologically, and on the other small enough that even taking recombination effects into account, an adequate charge, or in other words sufficiently charged particles, still reach the various measuring elements.

It is also preferred that the particles are charged in chronologically pulsed fashion. For a very brief period of time, the ionizing device is activated, and at the same time, a time measuring device is started. If an increase in detected charged particles is then recorded at the charge measuring device, the time measuring device is stopped. Thus in an especially simple way, the time in which the charged particles from the ionizing device reach the charge measuring device can be ascertained. Once again, the flow speed is obtained from the quotient of distance and time. Once again, the variant described above can be preferred with a plurality of measuring elements.

In addition, the invention can be refined such that the exhaust gas mass is ascertained or estimated from the measured charges. From the magnitude of the measured signal, a conclusion can be drawn about the charge quantity that has flowed past the charge measuring device. As a result, a quantitative statement is also possible with respect to the charge carriers that have flowed past and indirectly, a statement can be made about the quantity of exhaust gas that has flowed past.

BRIEF DESCRIPTION OF THE DRAWINGS

The invention will be described in further detail herein below, with reference to the drawings, in which:

Fig. 1a is a plan view schematically showing a first exemplary embodiment of a device according to the invention for measuring exhaust gas with charged particles;

FIG. 1b shows the first exemplary embodiment in a side view;

DESCRIPTION OF THE PREFERRED EMBODIMENTS

Figure 2:
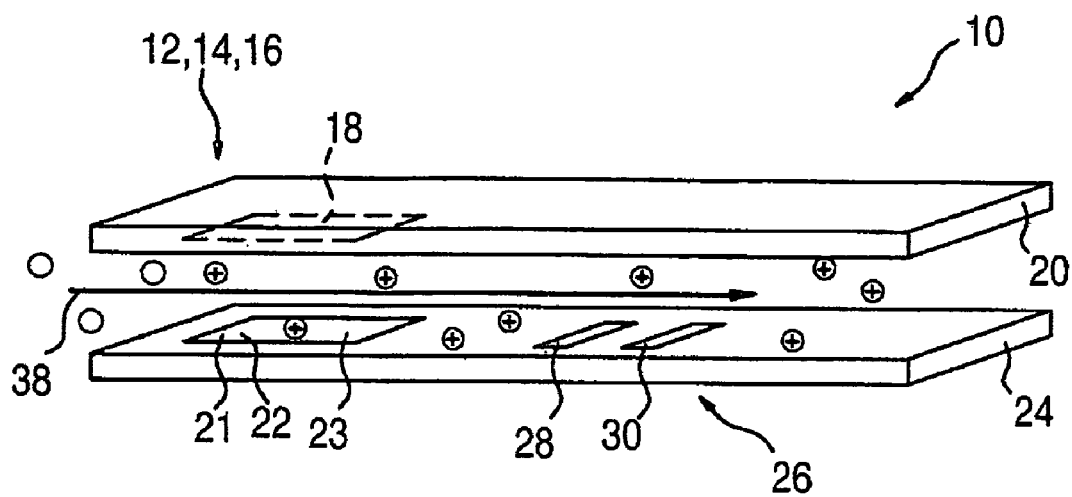
FIG. 2 shows a second exemplary embodiment.

FIGS. 1a and 1b show a device 10 for measuring exhaust gas using ionized particles. FIG. 1a shows the device 10 in plan view, and FIG. 1b shows the device 10 in a side view. The particles are represented symbolically by small circles, and ionized particles additionally have a "+" symbol. The device 10 has an ionizing device 12 with an electrode arrangement 14 having a pair of electrodes 16. The pair of electrodes 16 here comprises an antennalike electrode 18, which is disposed on a ceramic element 20 (in this case a two-layer ceramic substrate), and a two-dimensionally embodied counterelectrode 21, which is disposed in a sintered layer 25. In FIG. 1b, it can be seen clearly that the electrode 18 and counterelectrode 21 are spaced apart from one another, and that between them is a dielectric 23, which brings about the dielectrically impeded discharge. The device 10 furthermore has a charge measuring device 26, with a first and a second electrostatic electrode 28, 30. These electrostatic electrodes are disposed in the region of a heating element 32, which is heated by a heating coil 34. The heating element 32 is likewise located in the sintered layer 25. The electrical connections are embodied as terminal pads 36.

The mode of operation of the device 10 is in principle as follows: The exhaust gas flow 38, or a portion of it, is carried by way of the ceramic element 20. Particles and gas molecules are ionized, or ions are formed, by the electrode 18 and the counterelectrode 21. These charged particles move toward the charge measuring device 26, where they are detected first by the first electrostatic electrode 28 and then by the second electrostatic electrode 30. The signals of the electrostatic electrodes 28, 30, via the associated terminal pads 36, reach an evaluation device not identified by reference numeral. From the transit times between the ionizing device 12 and the first electrostatic electrode 28, between the ionizing device 12 and the second electrostatic electrode 30, and/or between the first and second electrostatic electrodes 28, 30 and the corresponding known distances, the exhaust gas flow speed can thus be determined. If needed, to simplify the construction, one of the electrostatic electrodes 28, 30 may also be omitted.

FIG. 2 shows a second exemplary embodiment, which is a coolant in its fundamental aspects to FIG. 1. The description thereof is accordingly referred to. However, here the electrode 18 has been disposed on a first ceramic element 20, and the counterelectrode 21 on a second ceramic element 24. Because of the two ceramic elements 20, 24 spaced apart from one another essentially parallel, the result is an advantageous exhaust gas course for carrying the exhaust gas into the region of the electrostatic electrodes 28, 30. Here, the counterelectrode 21, like the electrode 18, has been embodied two-dimensionally, so that high ionization energy can be brought to bear in a large interstice. Moreover, it is coated with an insulating layer 22.

Figure 3:
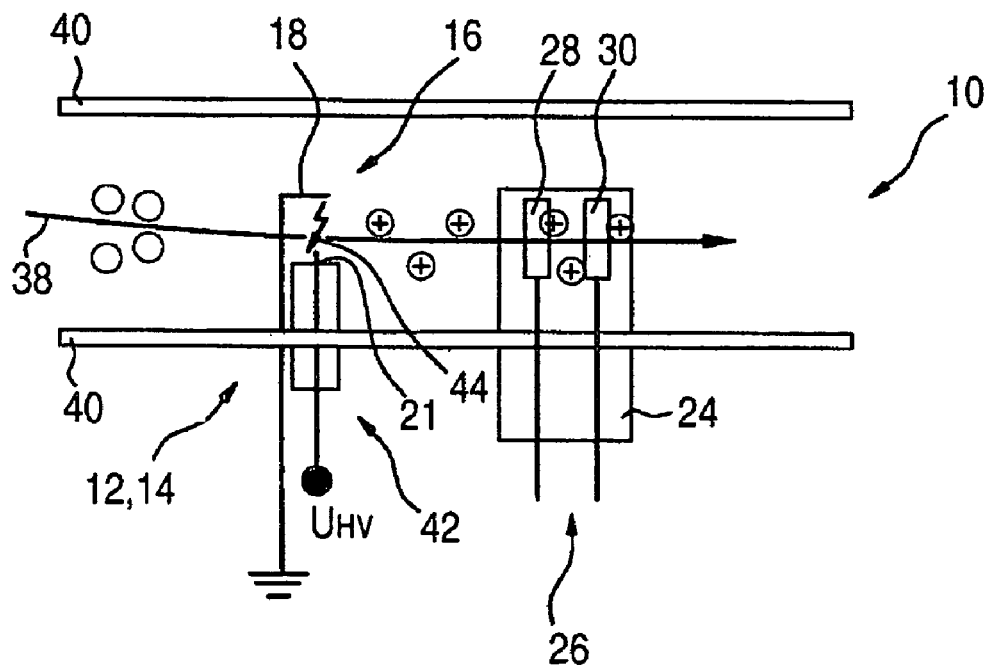
FIG. 3 shows a third exemplary embodiment.

In FIG. 3, a third exemplary embodiment is shown, in which the device 10 is disposed in an exhaust gas tube 40. Once again, for the principal mode of operation, see the descriptions of FIG. 1. The ionizing device 12 is realized here by a spark generator 42 on the principle of a spark plug. The spark generator 42 is operated in pulsed fashion by means of a high voltage $U_{HV}$, so that sparks 44 develop between the electrode 18 and the counterelectrode 21. This variant is especially economical.

The foregoing relates to a preferred exemplary embodiment of the invention, it being understood that other variants and embodiments thereof are possible within the spirit and scope of the invention, the latter being defined by the appended claims.

The invention claimed is:

1. A device for measuring exhaust gas with charged particles, the device comprising an ionizing device having an electrode arrangement and a charge measuring device, the electrode arrangement having at least one pair of electrodes including at least one electrode and at least one counterelectrode, and a dielectric to effect a dielectrically impeded discharge between the electrode and the counterelectrode, wherein the counterelectrode is disposed in a sintered layer, and wherein the device further comprises a first ceramic element and a second ceramic element, spaced apart from one another, the first and second ceramic elements defining an exhaust gas conductor.

2. The device as defined by claim 1, wherein the electrode and the counterelectrode each extend two-dimensionally.

3. The device as defined by claim 1, wherein the device is disposed in an exhaust gas tract.

4. The device as defined by claim 1, further comprising at least one ceramic element, and wherein the ionizing device and/or the charge measuring device is embodied on and/or inside at least one ceramic element.

5. The device as defined by claim 4, wherein at least portions of the ionizing device and of the charge measuring device are embodied on and/or inside a common ceramic element.

6. The device as defined by claim 4, further comprising at least one heating element.

7. The device as defined by claim 1, wherein at least portions of the ionizing device and of the charge measuring device are embodied on and/or inside a common ceramic element.

8. The device as defined by claim 7, further comprising at least one heating element.

9. The device as defined by claim 1, further comprising at least one heating element.

10. The device as defined by claim 9, wherein the heating element is disposed in the region of the charge measuring device.

11. A device for measuring exhaust gas with charged particles, the device comprising an ionizing device having an electrode arrangement and a charge measuring device, the electrode arrangement having at least one pair of electrodes including at least one electrode and at least one counterelectrode, and a dielectric to effect a dielectrically impeded discharge between the electrode and the counterelectrode, wherein the counterelectrode is disposed in a sintered layer and wherein the ionizing device comprises a spark generator operable on the spark plug principle.

12. A method for measuring exhaust gas with charged particles in which particles contained in the exhaust gas are charged by means of an ionizing device, and the charged particles are detected by means of a charge measuring device, the method comprising the steps of charging the particles by means of a dielectrically impeded discharge, measuring the charges, and ascertaining or estimating the exhaust gas mass from the measured charges, said method further comprising employing an evaluation device to determine a flow speed of the exhaust gas on the basis of a fixed spacing between the ionizing device and the charge measuring device.

13. The method as defined by claim 12, further comprising the step of charging the particles in chronologically pulsed fashion.

* * * * *